(12) United States Patent
Chubb et al.

(10) Patent No.: US 6,425,629 B1
(45) Date of Patent: Jul. 30, 2002

(54) VEHICLE ROOF FOR CONTROLLING LIGHT EXPOSURE OF THE SKIN

(76) Inventors: Charles R. Chubb, P.O. Box 1445, St. Charles, MO (US) 63302-1445; Lisa C. Rottler, 4560 Washington, Florissant, MO (US) 63033

(*) Notice: Subject to any disclaimer, the term of this patent is extended or adjusted under 35 U.S.C. 154(b) by 0 days.

(21) Appl. No.: 09/497,268

(22) Filed: Feb. 3, 2000

Related U.S. Application Data (60) Continuation-in-part of application No. 09/267,172, filed on Mar. 12, 1999, now abandoned, which is a division of application No. 08/572,110, filed on Dec. 14, 1995, now abandoned.

(51) Int. Cl.[7] .............................................. B60J 7/047
(52) U.S. Cl. .................................................. 296/215
(58) Field of Search ........................... 296/214, 215, 296/211, 224

(56) References Cited

U.S. PATENT DOCUMENTS 4,249,770 A * 2/1981 Hunt ........................... 296/218
4,852,938 A * 8/1989 Hirshberg et al. ........... 296/214
5,849,402 A * 12/1998 Kraemling et al. .......... 428/220
5,892,619 A * 4/1999 Chubb et al. ................ 359/361

FOREIGN PATENT DOCUMENTS

DE           3120431      * 12/1982 .................. 296/215

* cited by examiner

Primary Examiner—Dennis H. Pedder
(74) Attorney, Agent, or Firm—Henry W. Cummings (57) ABSTRACT

In accordance with the present invention, a vehicle roof with adjustable light transmitting sections to control the interior spectral radiation environment, including at least one first section for high ultraviolet transmission; and, at least one second section for high transmission of visible and infrared light while blocking part of the ultraviolet radiation; a frame to hold said first and second sections in place; and means for positioning said sections relative to each other. In another embodiment a third section is provided with differing spectral transmission than said first and second sections is provided together with means for moving said third section relative to said first and second sections.

19 Claims, 5 Drawing Sheets

VEHICLE ROOF FOR CONTROLLING LIGHT EXPOSURE OF THE SKIN

REFERENCE TO RELATED APPLICATIONS

This application is a continuation-in-part of application Ser. No. 09/267,172, file Mar. 12, 1999, now abandoned which is division of application Ser. No. 08/572,110 filed Dec. 14, 1995, now abandoned.

FIELD OF THE INVENTION

The present invention relates to vehicles roof and a method and apparatus to adjust the light exposure of the skin through the vehicle roof.

BACKGROUND OF THE INVENTION

The present invention relates to an adjustable ultraviolet transmission vehicle sunroof with translational elements to transmit, partially transmit, or block solar ultraviolet radiation. This allows persons in the vehicle to obtain additional potentially beneficial ultraviolet exposure in the fall and winter or other times when a deficiency in exposure is common. It also allows persons in the vehicle to protect themselves from possibly harmful ultraviolet radiation in the spring and summer or other times when overexposure is common. The exposure can be adjusted according to the skin type and needs of the individuals in the vehicle.

Convertibles provide good visibility, enjoyable exposure to sunlight, fresh air and a feeling of spaciousness. However, the hazard in accidents has led to a variety of modifications including Increasingly popular sunroofs. The nearly universal use of vehicle air conditioners has resulted in many persons having the windows closed not only when it is cold in the winter but also when it is warm or hot in the summer. Since the windows block the biologically active ultraviolet radiation, persons with a deficiency in exposure miss a possibly beneficial exposure especially in the fall and winter when an underexposure is common. Some have proposed the use of ultraviolet transmitting glazing to obtain full spectrum solar radiation exposure. However, there is an associated potential hazard of increasing the risk of sunburn and skin cancer, especially for light skin persons living in bright areas such as Australia.

An open sunroof with direct exposure to sunlight is an obvious hazard. The hazard of sunlight is so well publicized some may be over reacting and not obtaining sufficient sunlight as discussed by Ness and debated by many. The ultraviolet protection afforded by common glass is recognized by most persons. The use of ultraviolet glazing for vehicles as proposed by Wendel and Downing requires great care to avoid potential hazards. Light and dark skin persons have greatly different tolerances and needs.

The ultraviolet transmitting glass looks just like glass that blocks the ultraviolet radiation so the hazard is hidden. Skin cancer in animals can be produced by suberythemal daily doses. One would expect humans likewise may develop skin cancer by a series of daily doses none of which cause a noticeable reddening of the skin. The skin cancer may occur long after the exposure. In addition, a large dose of vitamin D significantly reduces depression and improves the mood, Gloth. Thus sunlight induced vitamin D is reasonably expected to reduce depress,ion and improve the mood just as is generally experienced in the spring.

The combination of hidden hazard, delayed occurrence of effects and increased feeling of well being make great care necessary in the initiation of the use of ultraviolet transmitting glazing for vehicles. Precautions such as government regulations requiring a slight noticeable unique color tint or other distinguishing easily-noticeable feature for ultraviolet transmitting glazing may be expected.

There are many difficulties in initiating the use of ultraviolet transmitting glazing. However, as pointed out by Ness there is some possibility of reductions in the extent of diseases such as coronary heart disease and some types of cancer. Darker areas tend to have higher incidences of these diseases. Thus the time of the year to increase exposure is when underexposure is common, the fall and winter. Fortunately, the time of year when overexposure is common is the rest of the year. Using ultraviolet transmitting glazing during the dark part of the year and ultraviolet blocking or partially blocking glazing during the rest of the year is a reasonable approach. There is a possibility of both obtaining the benefits of an additional light exposure and avoiding an increased risk of sunburn and skin cancer.

Some prior art includes the proposed use of ultraviolet transmitting glazing. The use of full spectrum transmission to wavelengths as short as 280 nm is sometimes listed including references to Professor Hollwich. Professor Hollwich proposes the solar spectrum is best and through the eyes light maintains a proper hormone and metabolic balance. In a recent publication he described how removal of cataracts (which were blocking sufficient irradiation of the retina) restored proper metabolic balance. Since the skin responds to wavelengths near 290 nm while these wavelengths are filtered out before reaching the retina, full spectrum irradiation for health includes both effects of skin exposure at short wavelengths and through-the-eyes exposure of the retina for longer wavelengths.

The full spectrum theory that natural sunlight is best can be oversimplified in application in some subtle ways. For example, migration has resulted in persons living in areas not well suited for their skin type. Whites with countries of origin of their ancestors in northern latitudes are living in bright areas such as Australia. Blacks with countries of origin of their ancestors near the equator are living in areas with little sunlight in the winter.

The solar radiation environments near the equator as compared with the environments at higher latitude have several differences. Near the equator the length of the day doesn't change much throughout the year. At noon the sun is relatively high in the sky. In contrast at higher latitudes the length of the day is short in the winter, long in the summer and the sun is not very high in the sky in winter at noon.

The equatorial clear day visible light is not greatly different than that in the summer at higher latitudes. The sun is relatively high in the sky near noon during the summer over a relatively large range it latitudes. The visible attenuation doesn't change greatly with sun elevation. For ultraviolet radiation the attenuation by the atmosphere is much greater than for visible light. At high latitudes the ultraviolet radiation varies greatly with the season and latitude. Near the equator the clear day ultraviolet radiation is high and doesn't change much with season (WHO-160, listed in references).

The overall effect is blacks have a skin adapted for a relatively constant and high level ultraviolet environment. Whites have a skin'suitable for very low ultraviolet radiation in the winter. Some whites have little capability for tanning for protection in the summer while others tan and bleach effectively.

Blacks at high latitudes generally have a large deficiency in ultraviolet exposure in the winter. Whites at low latitudes generally have a large ultraviolet overexposure during the summer. This applies not only to the skin but also to the eyes. Blacks usually have dark highly attenuating eyes. Many whites have light-colored low attenuating eyes.

Thus when controlling the light environment just providing full spectrum transmission or lighting can be an oversimplification. Adjusting the visible and ultraviolet environment depends on the time of year and an individuals skin type. It also depends on the occupation and skin exposure habits. An office worker usually has greater needs for additional light than an outdoor worker. A person with gardening or outdoor sports as a hobby usually has less need for supplemental exposure.

The skin exposure of an individual needs to be controlled with the objective of both avoiding overexposure (decreasing the risk of sunburn and skin cancer) and obtaining sufficient exposure during the rest of the year to increase the probability for good health. Full spectrum transmission is an oversimplification and needs to be modified depending on a persons skin type, sun exposure habits and the local environment.

Prior art for vehicle ultraviolet transmitting glazing, conventional glazing and vehicles sunroofs includes patents by: Downing: GB 2 196 625, Wendel: DE 31 20 431 A1, Goldner: DE 197 22 722 A1, Hirshberg: U.S. Pat. No. 4,852,938, Lutz: U.S. Pat. No. 4,626,023, Hunt: U.S. Pat. No. 4,249,770, Candler Jr.: U.S. Pat. No. 2,489,751, Lynam: U.S. Pat. No. 5,239,406, and Kraemling: U.S. Pat. No. 5,849,402.

Downing, Nicholas P. D.: GB 2 196 625, May 5, 1988. Ultra violet transmitting means. The invention provides for the use of ultraviolet light transmitting glass for example as glazing for buildings and motor vehicles to allow the transmission of a greater amount of the ultraviolet light into such buildings and motor cars to enhance the health promoting effects on humans in such buildings and motor cars.

Wendel, H.: DE 3120-431 A1, May 22, 1981. Biologically effective glazing for vehicles—has window glass and vehicle roof replaced by glazing material which does not cut out part of the spectrum. The biologically effective glazing of motor cars, trains and omnibusses is achieved by replacing existing vehicle windows, which allow only part of the spectrum of light to pass, by a material such as Acrylglass (RTM) 2028 or 080 quartzglass which allow all the spectrum to pass. Part of the roof can be replaced by a fixed or sliding cover of the new material. This avoids damage to the hormone balance of the body through being exposed only to a part light spectrum. The claims include attenuation or total blocking by blinds, automatic control of brightness with a photocell or use of phototropic material.

Goldner, Horst H.: DE 197 22 722 A1, May 30, 1997. Protection apparatus to cover/uncover windows, especially a sunshade apparatus for an auto roof. This invention includes flexible material between window shade type rollers. The material can be unrolled or rolled back up to provide a shading or visible light transmission with ultraviolet blocking. Multiple rollers and multiple strips can be use when necessary to fit within a curved auto roof.

Hirshberg, Gerald P.: U.S. Pat. No. 4,852,938, Aug. 1, 1989. Transparent roof convertible automobile with retractable sunshade. An autobody is provided with a transparent roof panel that slides rearwardly from a normal position in which it closes a roof opening of the body, to a retracted position in which it overlies a rear window of the body. When the transparent roof is in its normal position in which it closes the roof opening, the sunshade,may be manually slid back and forth to overlap varying portions of the transparent roof panel. Fingers, (52 and 54 in patent drawing) prevent the shade sections from being moved forward when the transparent roof panel is retracted so the shades can't be blown off by the wind when the car is in motion.

Lutz, Alfons: U.S. Pat. No. 4,626,0023, Jun. 20, 1984. Sliding roof having a sliding inside roof lining. A sliding roof for motor vehicles having a transparent rigid sliding cover by means of which an opening in the roof can be selectively closed or can be exposed at least partially. A frameless sliding inside cover lining is provided that can be displaced at least in the cover sliding direction independently from the sliding cover and is guided at its lateral edges. The inside cover is specially designed to avoid binding preventing movement upon heating in the summer.

Hunt, Keith R.: U.S. Pat. No. 4,249,770, Feb. 10, 1981. Vehicle opening roofs. A vehicle opening roof comprises a frame which surrounds a longitudinal opening in the roof of a vehicle and a panel assembly which is guided between spaced parallel guide rails forming the side members of the frame. Clamp shoes can lock the panel in an intermediate open, position.

Candler, G. V. Jr.: U.S. Pat. No. 2,489,751, Jul. 26, 1945. Roof or covering. An object of this invention is to provide a roof of transparency material and to vary or modify its transparency characteristics selective from clear transparency to absolute opaque to thereby control both the heat and light transfer properties of the material. The figure shows a four door sedan with the entire roof of transparent material in two layers. Either mercury or India ink is forced into the gap between the transparent layers to form either a reflecting or black absorbing roof surface.

Lynam, Niall R.: U.S. Pat. No. 5,239,406, Jul. 18, 1991. Near infrared reflecting, ultraviolet protected, safety protected, electrochromic vehicular glazing. A vehicle glazing with electric field control of light transmittance. Ultraviolet protection of the electrochromic material is provided.

Kraemling, Franz: U.S. Pat. No. 5,849,402, Jun. 19,1995. Laminated pane with low energy transmission. A pane having a laminated structure, comprising at least one sheet of tinted glass, and at least one sheet of polymeric material containing a UV-absorbing agent. The ultraviolet transmission factor is less than 0.5%. The total thickness of the pane is from 2.5 to 8 mm.

Prior art review—The use of full spectrum glazing by Wendel and Downing does not include the special deviations from full spectrum transmission needed during part of the year to avoid increasing the risk of sunburn and skin cancer.

The sliding sunroofs of Hirshberg, Lutz and Hunt do not provide discrete selectable positioning needed for ultraviolet transmission selection as does a set of holes with retractable pins. Selectable positioning is needed for calibration and use of the vehicle roof.

The optical switch method of Candler Jr. uses materials such as mercury now known to be very toxic, Massaro. If an optical switch device similar to the Candler arrangement is used for the present application without mercury the transparent material must transmit the ultraviolet radiation. If an ultraviolet absorbing liquid leaks out then the failure leaves the roof in an undesirable hazardous condition increasing the risk of sunburn and skin cancer. Also, this type of switch does not easily provide intermediate ultraviolet transmission values.

The Goldner technique using flexible material on rollers provides shading or visible transmission with ultraviolet blocking. By changing materials a similar device could provide visible light transmission with UV transmission or with UV blocking. However, thin sheets of flexible material on a roller drive are not likely to be as reliable and durable as two solid panes of glass or plastic.

The Lynam electrical field control of light transmittance includes protection of the electrochromic material from ultraviolet radiation. This type of device might be used to control visible light when the UV radiation is blocked. To use a similar device for UV control, electrochromic material not needing UV protection and a special design for UV switching would be required. Reliability, weathering, durability and cost are potential problems compared to the use of two panes of glass or plastic.

The Kraemling type laminated pane should be suitable for use as a UV-blocking low-energy-transmitting element.

DESCRIPTION OF THE PREFERRED EMBODIMENTS

Figure 1:
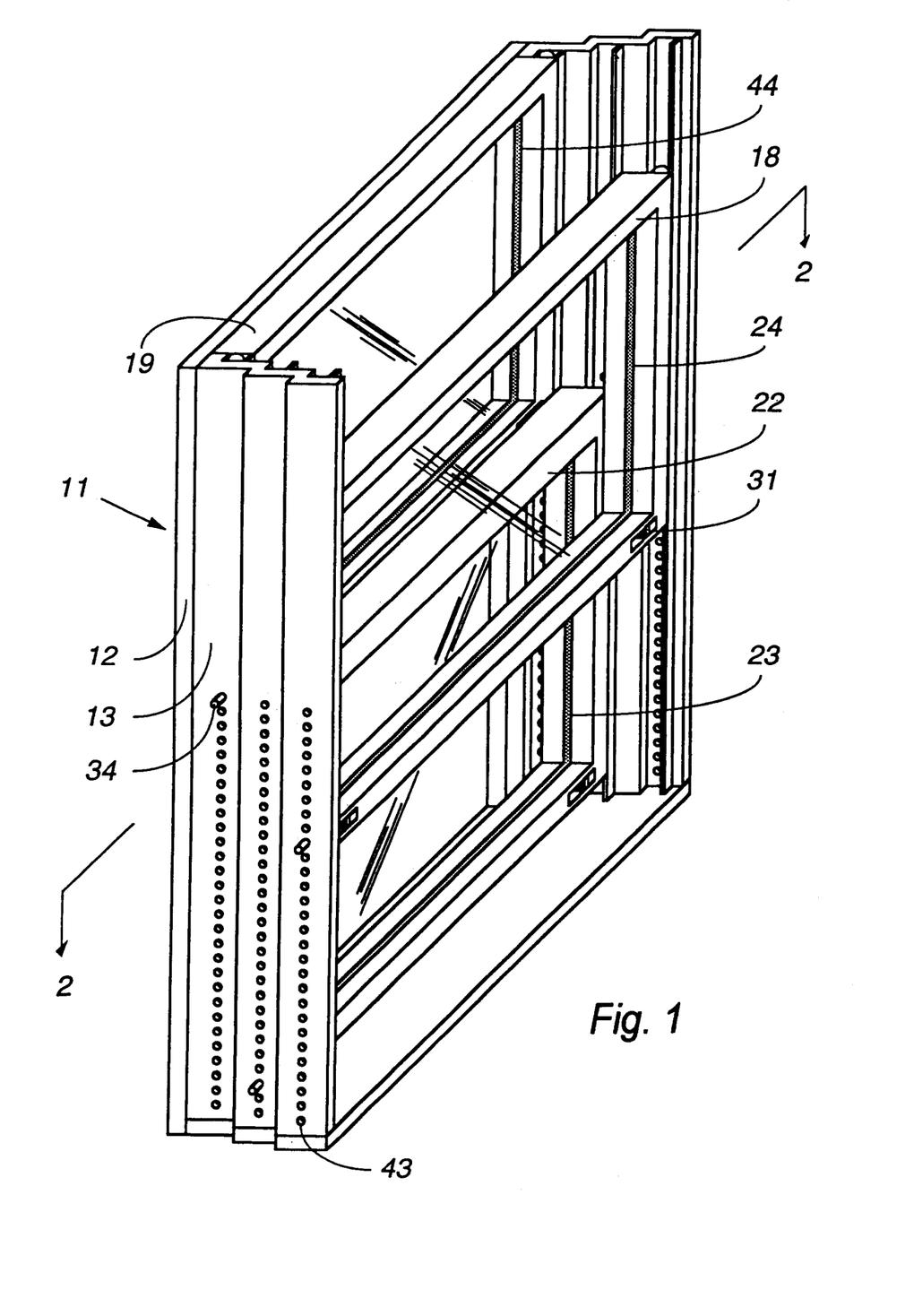
FIG. 1 is a perspective view of an adjustable ultraviolet transmission window.
Figure 2:
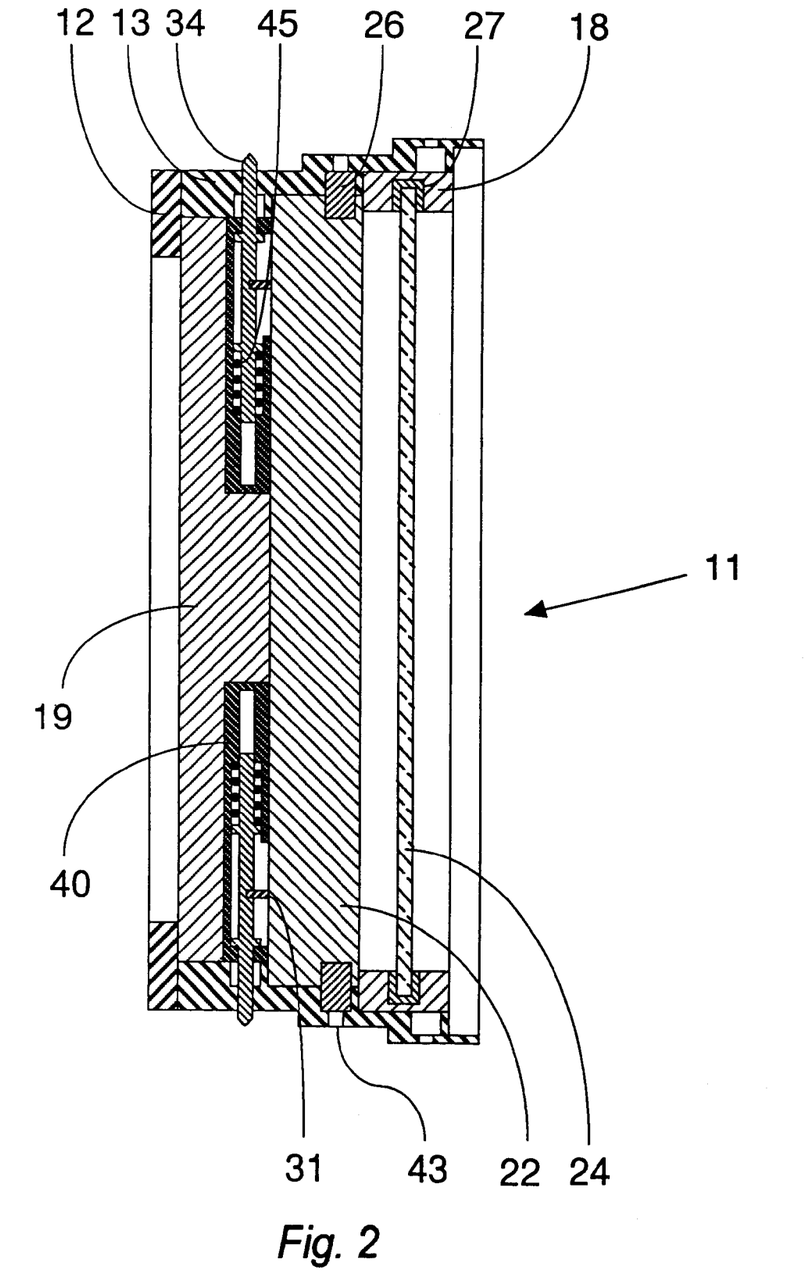
FIG. 2 is a sectional view of the adjustable ultraviolet transmission window.

The above and other objects and advantages and novel features of the present invention will become apparent from the following detailed description of the preferred embodiment of the invention illustrated in the accompanied drawings, wherein:
Adjustable Ultraviolet Transmission Window FIG. 1 illustrates an adjustable window, 11, of know construction which is currently available. The sections are positioned for intermediate ultraviolet transmission;

Referring now to the sectional view in FIG. 2, the outer frame, 12, along with the side supports, 13, are used to support the movable windows 19, 22, and 18. The ultraviolet transmitting window is the outer window, 19. The windows in the middle, 22, and inner unit, 18, block the ultraviolet UV-B (280–315 nm) radiation.

A window insert, 24, is held by a grommet, 27 (FIG. 2). The window is guided along the track by the guide, 26. The retractable pins, 34, enable the window to be positioned manually using the handles, 31. The pins are held engaged in positioning holes, 43, by the springs, 45, located in holders 40.

Referring now to FIG. 1, for maximum ultraviolet transmission, the inner window, 18, is lowered so the outer ultraviolet transmitting window, 19, is unobscured. For maximum blocking of the ultraviolet radiation the inner window, 18, is raised to the top to block the ultraviolet radiation passing through the outer window, 19. For intermediate ultraviolet transmission, the inner window, 18, is positioned at an intermediate position as illustrated in FIG. 1.

The UV transmitting window, 19 (FIG. 1) has an insert, 44, composed of material that is substantially transparent to light rays from the ultraviolet, visible, and part of the infrared solar spectrum. The UV blocking sections, 18, and 22, are substantially transparent to the visible and infrared solar radiation. The side frames, 13, hold the windows and allows them to be positioned for high, intermediate or very low radiation transmission.

To raise or lower a window, the two positioning pin handles, 31, (FIG. 1) are moved toward each other by actuator means to release the pins from the positioning holes freeing the window. The window is then moved up or down by actuators, and the pins are released when the window is in the desired position. When the pins engage the holes, the window is held in place and the actuators can be released.

Figure 3:
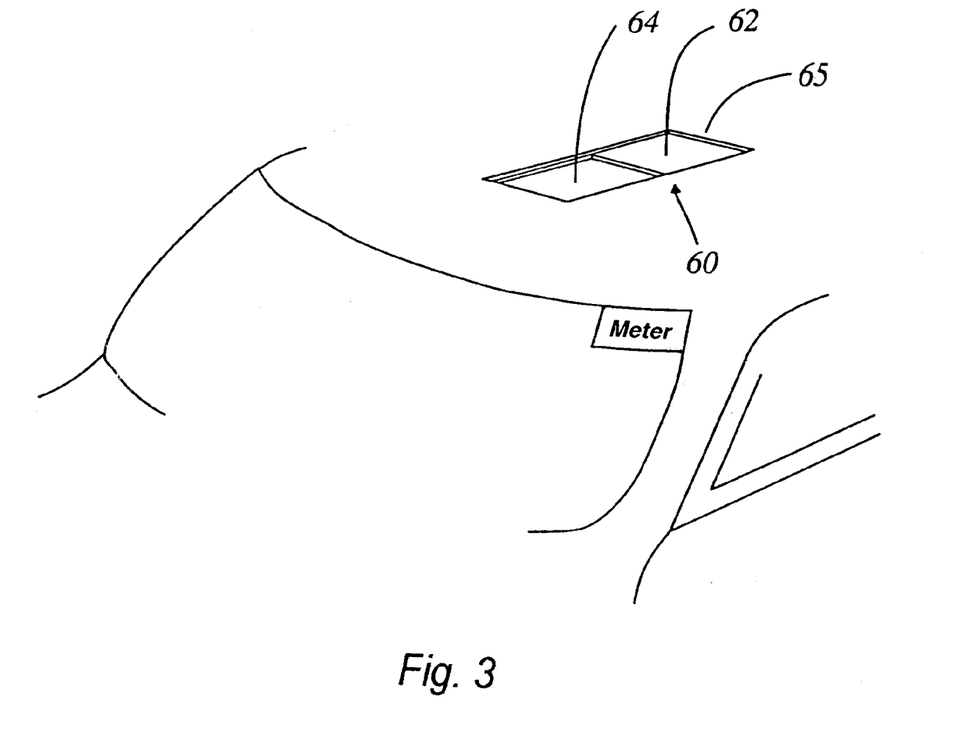
FIG. 3 is a perspective of the vehicle ultraviolet roof for controlling light exposure of the skin.

The material of which the ultraviolet transmitting window, 19, insert, 44, (FIG. 1) is composed is an optically transmitting material such as ultraviolet transmitting glass or plastic similar to the materials described by Driscoll and by Sliney, hereby incorporated into the present application by this reference. Briefly the materials are
Adjustable Ultraviolet Transmission Sunroof FIG. 3 illustrates an adjustable ultraviolet transmission sunroof, 65, for a vehicle, 60. The outer element, 62, is ultraviolet diffusely transmitting material. The inner sliding element, 64, blocks the ultraviolet radiation and attenuates the visible light. By positioning an inner sliding element the ultraviolet transmission can be adjusted. The method of operation is similar to the window in FIG. 1. The inner section, 64, is partially transparent to visible light to avoid glaring bright light transmission when the sun is overhead.

A person receiving too little or too much ultraviolet B radiation can adjust the sunroof, 65, for appropriate UV-B transmission. A person receiving sufficient UV-B radiation while outside the vehicle can position the sliding element to block the ultraviolet B radiation.

Figure 4:
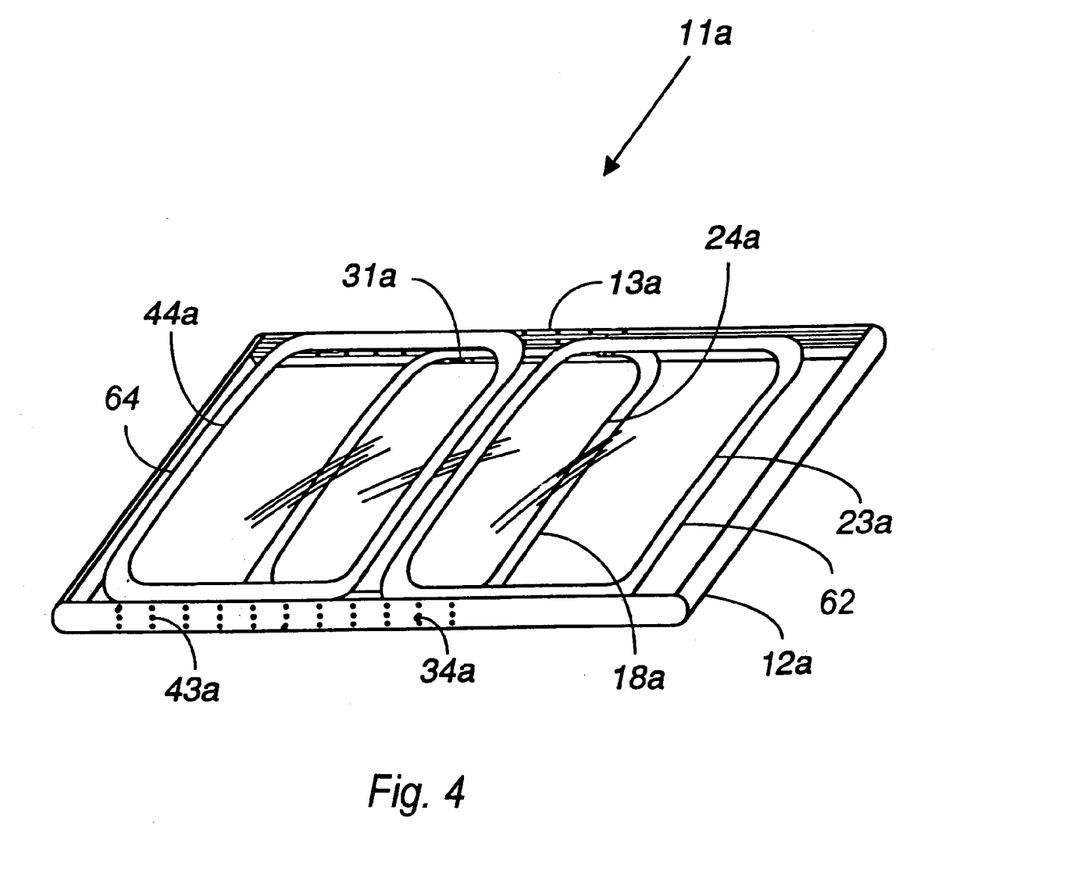
FIG. 4 is a detail perspective view of the vehicle ultraviolet roof.

Referring now to the view in FIG. 4, the frame, 12a, including the side supports, 13a, is used to support the movable windows, 62, 64, and 18a. The ultraviolet transmitting window is the outer window, 62. The other windows, 64 and 18a, block the ultraviolet UV-B (280–315 nm) radiation.

In window 18a insert, 24a, and in window 64 insert, 23a, are held by grommets. The windows are movable along the track. The retractable pins, 34a, enable the window to be positioned using handles similar to those in FIG. 2. The glasses such as Pyrex, trademark, that transmit a fraction of the ultraviolet B radiation and are not extremely high in cost. Other glasses such as Vycor, trademark, and fused silica transmit a higher fraction of the ultraviolet radiation but the cost is prohibitive for many applications. Plastic materials such as Plexiglas, trademark, have high transmission in the UV-B. However, many of the plastic materials are not solar resistant and darken upon long term exposure to sunlight and are satisfactory only for low exposure.

The material of which the ultraviolet B radiation blocking inserts, 23 and 24, (FIG. 1) are composed is conventional window glass or plastic.

The general UV-B non-direct solar radiation environment in a room is increased when the UV-B transmitting area is increased. In any area with direct solar irradiation through a specularly transparent window the area irradiated by UV-B is increased When the UV-B transmitting area is increased. The direct irradiation is not altered. The risk of overexposure is reduced by the use of a diffusely UV-B transmitting window 19, insert, 44, (FIG. 1) of the preferred embodiment.

A meter can be used to measure the ultraviolet solar radiation transmitted by the window. Estimates of the appropriate exposure for a person with particular skin type are needed to determine the exposure time for window transmitted ultraviolet B radiation. handles, 31a, are located near the sides of the windows. The pins are held engaged in positioning holes, 43a, by springs similar to those shown in FIG. 2.

Referring now to FIG. 4, for maximum ultraviolet transmission, the window, 18a, is moved all the way to the right so the outer ultraviolet transmitting window 62 is unobscured. To block the ultraviolet radiation the window 18a, is moved all the way to the left. For intermediate ultraviolet transmission, the window, 18a, is positioned at an intermediate position as illustrated in FIG. 4.

The UV transmitting window, 62, has an insert, 44a, composed of material that is substantially transparent to light rays from the ultraviolet, visible, and part of the infrared solar spectrum. The UV blocking section, 18a and 64, are transparent to the visible and infrared solar radiation. The side frames, 13a, hold the windows and allow them to be positioned for high, intermediate or very low ultraviolet radiation transmission.

Figure 5:
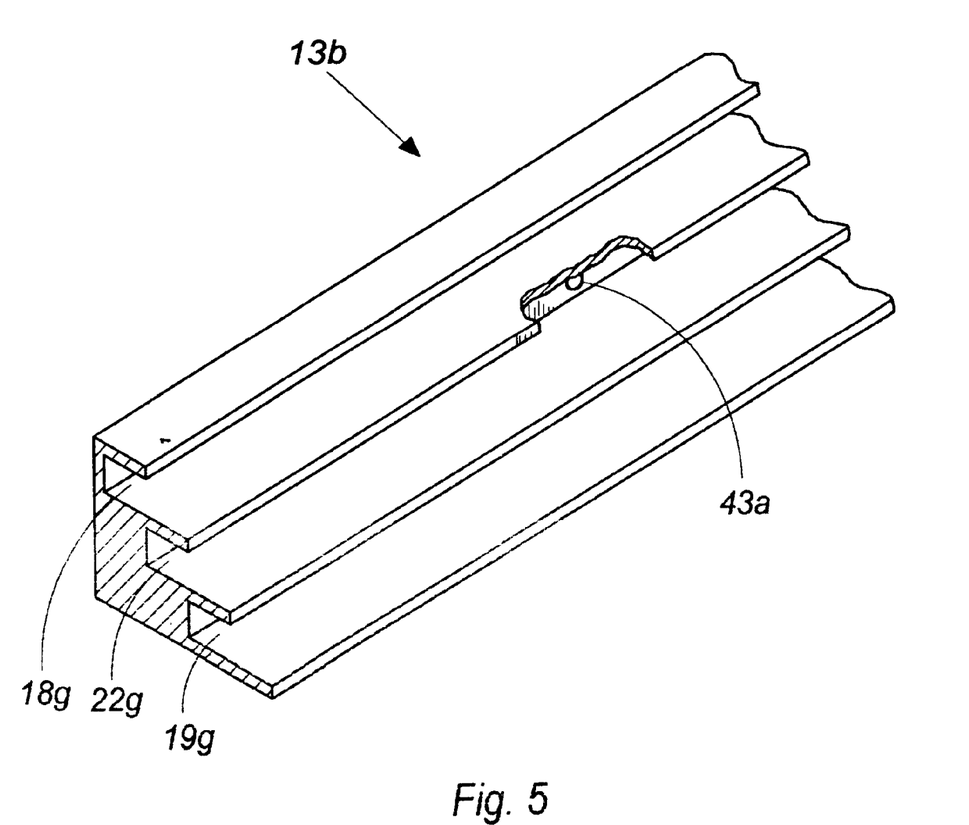
FIG. 5 is a sectional view of the side rail of the vehicle ultraviolet roof.

Recessed grooves, 18g, 22g, and 19g shown in FIG. 5 hold the windows, 18a, 64 and 62. The holes 43a enable the windows to be positioned at selected locations.

References Cited

U.S. PATENT DOCUMENTS

Candler Jr. U.S. Pat. No. 2,489,751
Hunt U.S. Pat. No. 4,249,770
Lutz U.S. Pat. No. 4,626,023
Hirshberg U.S. Pat. No. 4,852,938
Lynam U.S. Pat. No. 5,239,406
Kraemling U.S. Pat. No. 5,849,402.

OTHER PATENT DOCUMENTS

Downing GB 2 196 625
Wendel DE 31 20 431 A1
Goldner DE 197 22 722 A1

OTHER REFERENCES

Gloth, Michael: Vitamin D and seasonal affective disorder. Journal of Nutrition, Health and Aging, vol.3 (1) 5–7:1999.
Ness, A. R.: Are we really dying for a tan? British Medical Journal 1999;319:114–116 (10 July).and e-responses.
Hollwich, F.: The influence of light via the eye on metabolism and hormones. Klin Monatsbl Augenh 195: (5) 284–290 November 1989.
Massaro, Edward J.: Handbook of Human Toxicology. 1997, CRC Press, Boca Raton, p163.
World Health Organization (WHO): Environmental Health Criteria 160, Ultraviolet Radiation. Geneva, 1994, p22–23.
Driscoll, W. G., Editor: Handbook of Optics, Optical Society of America, McGraw Hill Company, New York, 1978. Pages 7–24 and 8–32.
Sliney, D. and M. Wolbarsht: Safety with Lasers and other Optical Sources. Plenum Press, New York, 1980. Page 495.

What is claimed is:

1. A vehicle roof with adjustable light transmitting sections to control the interior spectral radiation environment comprising: a roof body portion extending between a front and a rear portion of a vehicle; said roof body portion including at least one first section transmitting visible light and ultraviolet radiation including ultraviolet B radiation; at least one second section transmitting visible light while blocking essentially all ultraviolet UVB radiation; a frame to hold said first and second sections in place; means for measuring the radiation transmitted into the vehicle; and means for positioning said sections relative to each other.

2. A vehicle roof according to claim 1 comprising a third section with differing spectral transmission than said first section and means for moving said third section relative to said first and second sections.

3. A vehicle roof according to claim 2 wherein said first section for ultraviolet transmission is the outer most window.

4. A vehicle roof according to claim 3 wherein said first section for ultraviolet transmission is the outer most window and said second section for transmission of visible and infrared light while blocking part of the ultraviolet radiation is located below said first section.

5. A vehicle roof according to claim 4 wherein said second section is the inner most window.

6. A vehicle roof according to claim 5 wherein said second section is the middle window between said first and third sections.

7. A vehicle roof according to claim 2 wherein said second section is the bottom window located below said first and third sections.

8. A vehicle roof according to claim 1 wherein the means for positioning said first section relative to said second section includes retractable pins.

9. A vehicle roof according to claim 8 wherein at least one handle is provided to move said retractable pins.

10. A vehicle roof with adjustable light transmitting sections to control the interior spectral radiation environment comprising: a roof body portion extending between a front and a rear portion of a vehicle; said roof body portion including at least one first section transmitting visible light and ultraviolet radiation including ultraviolet B radiation; at least one second section transmitting visible light while blocking essentially all ultraviolet UVB radiation; a frame to hold said first and second sections in place; means for measuring the radiation transmitted into the vehicle; and means for positioning said sections relative to each other, and wherein said first ultraviolet transmitting section is the inner most section.

11. A method to control the interior spectral radiation environment comprising: providing a vehicle roof having a roof body portion extending between a front and a rear portion of a vehicle; said body portion including adjustable light transmitting sections including at least one first section transmitting visible light and ultraviolet radiation including ultraviolet B radiation; at least one second section transmitting visible light while blocking essentially all ultraviolet UVB radiation; measuring the radiation transmitted into the vehicle; and repositioning said first and second sections relative to each other to control interior spectral radiation.

12. A method according to claim 11 comprising providing a third section with differing spectral transmission than said first section and repositioning said third section relative to said first and second sections to control interior spectral radiation.

13. A method according to claim 12 including locating in said roof said first section for ultraviolet transmission as the outer most window.

14. A method according to claim 12 including locating in said roof said first section for ultraviolet transmission as the inner most window.

15. A method according to claim 12 including locating said first the ultraviolet transmitting section as the outer most window.

16. A method according to claim 12 including locating said first section for ultraviolet transmission as the outer most window and locating said second section for transmission of visible and infrared light while blocking part of the ultraviolet radiation below said first section.

17. A method according to claim 16 including locating said second section as the inner most window.

18. A method according to claim 16 including locating said second section as the middle window between said first and third sections.

19. A method to control the interior spectral radiation environment comprising: providing a vehicle roof having a roof body portion extending between a front and a rear portion of a vehicle; said body portion including adjustable light transmitting sections including at least one first section transmitting visible light and ultraviolet radiation including ultraviolet B radiation; and at least one second section transmitting visible light while blocking essentially all ultraviolet UVB radiation; measuring the radiation transmitted into the vehicle; and repositioning said first and second sections relative to each other to control interior spectral radiation; and wherein said first ultraviolet transmitting section is the inner most section.

\* \* \* \* \*